(12) United States Patent
Lacza et al.

(10) Patent No.: US 10,111,906 B2
(45) Date of Patent: Oct. 30, 2018

(54) SERUM FRACTION OF PLATELET-RICH FIBRIN

(71) Applicant: Lacerta Technologies Inc., Raleigh, NC (US)

(72) Inventors: Zsombor Lacza, Csopak (HU); Gabriella Vácz, Paks (HU)

(73) Assignee: Lacerta Technologies Inc., Raleigh, NC (US)

( * ) Notice: Subject to any disclaimer, the term of this patent is extended or adjusted under 35 U.S.C. 154(b) by 0 days.

(21) Appl. No.: 15/283,576

(22) Filed: Oct. 3, 2016

(65) Prior Publication Data

US 2017/0035809 A1 Feb. 9, 2017

Related U.S. Application Data

(62) Division of application No. 14/178,573, filed on Feb. 12, 2014, now Pat. No. 9,480,716.

(60) Provisional application No. 61/763,504, filed on Feb. 12, 2013.

(51) Int. Cl.
| | |
|---|---|
| *A61K 35/19* | (2015.01) |
| *A61L 27/36* | (2006.01) |
| *A61K 35/16* | (2015.01) |
| *A61L 27/38* | (2006.01) |
| *A61L 27/52* | (2006.01) |

(52) U.S. Cl.
CPC ............ *A61K 35/19* (2013.01); *A61K 35/16* (2013.01); *A61L 27/3616* (2013.01); *A61L 27/38* (2013.01); *A61L 27/52* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | |
|---|---|---|
| 2004/0213777 A1 | 10/2004 | Baugh et al. |
| 2008/0044852 A1 | 2/2008 | Kanayinkal et al. |
| 2009/0047242 A1 | 2/2009 | Reinecke et al. |
| 2011/0135698 A1 | 6/2011 | Lundquist et al. |
| 2012/0027740 A1 | 2/2012 | Philippart |
| 2013/0243878 A1 | 9/2013 | Mariner et al. |

OTHER PUBLICATIONS

Anitua et al., "Plasma rich in growth factors: preliminary results of use in the preparation of future sites for implants", Int. J Oral Maxillofac. Implants, 1999, vol. 14(4), p. 529-535, Abstract Only.
Chen Yao Su et al., "In vitro release of growth factors from platelet-rich fibrin (PRF): a proposal to optimize the clinical applications of PRF", Oral Surg Oral Med Oral Pathol Oral Radiol. Endod, 2009, vol. 108, No. 1, p. 56-61.
Araki et al., "Optimized Preparation Method of Platelet-Concentrated Plasma and Noncoagulating Platelet-Derived Factor Concentrates: Maximization of Platelet Concentration and Removal of Fibrinogen", Tissue Engineering: Part C, 2012, vol. 18(3), p. 176-185.
Burnouf et al., "Human blood-derived fibrin releasates: Composition and use for the culture of cell lines and human primary cells", Biologicals, 2012, vol. 40, p. 21-30.
Chien et al., "Incorporation of exudates of human platelet-rich fibrin gel in biodegradable fibrin scaffolds for tissue engineering of cartilage", J Biomed Mater Res Part B, 2012, vol. 100B, p. 948-955.
Dohan et al., "Platelet-rich fibrin (PRF): A second-generation platelet concentrate", Oral Surg Oral Med Oral Pathol Dral Radiol Endod, 2006, vol. 101, p. E37-44.
Ehrenfest et al., "In Search of a Consensus Terminology in the Field of Platelet Concentrates for Surgical Use: Platelet-Rich Plasma (PRP), Platelet-Rich Fibrin (PRF), Fibrin Gel Polymerization and Leukocytes", Current Pharmaceutical Biotechnology, 2012, vol. 12, p. 1131-1137.
Kang et al., "Platelet-Rich Fibrin is a Bioscaffold and Reservoir of Growth Factors for Tissue Regeneration", Tissue Engineering, Part A, 2011, vol. 17(3 & 4), p. 349-359.

*Primary Examiner* — Kade Ariani
(74) *Attorney, Agent, or Firm* — Jason D. Voight

(57) ABSTRACT

The invention provides for a method of preparing an isolated serum fraction of platelet rich fibrin (PRF), comprising the steps of
  a. providing platelet rich plasma (PRP) without the addition of an anticoagulant;
  b. clotting the PRP to obtain a coagel of PRF; and
  c. separating the coagel to isolate the serum fraction which comprises an activated platelet releasate;
and further provides for the isolated serum fraction obtained by such method, and its medical use.

22 Claims, 4 Drawing Sheets

SERUM FRACTION OF PLATELET-RICH FIBRIN

Figure 1:
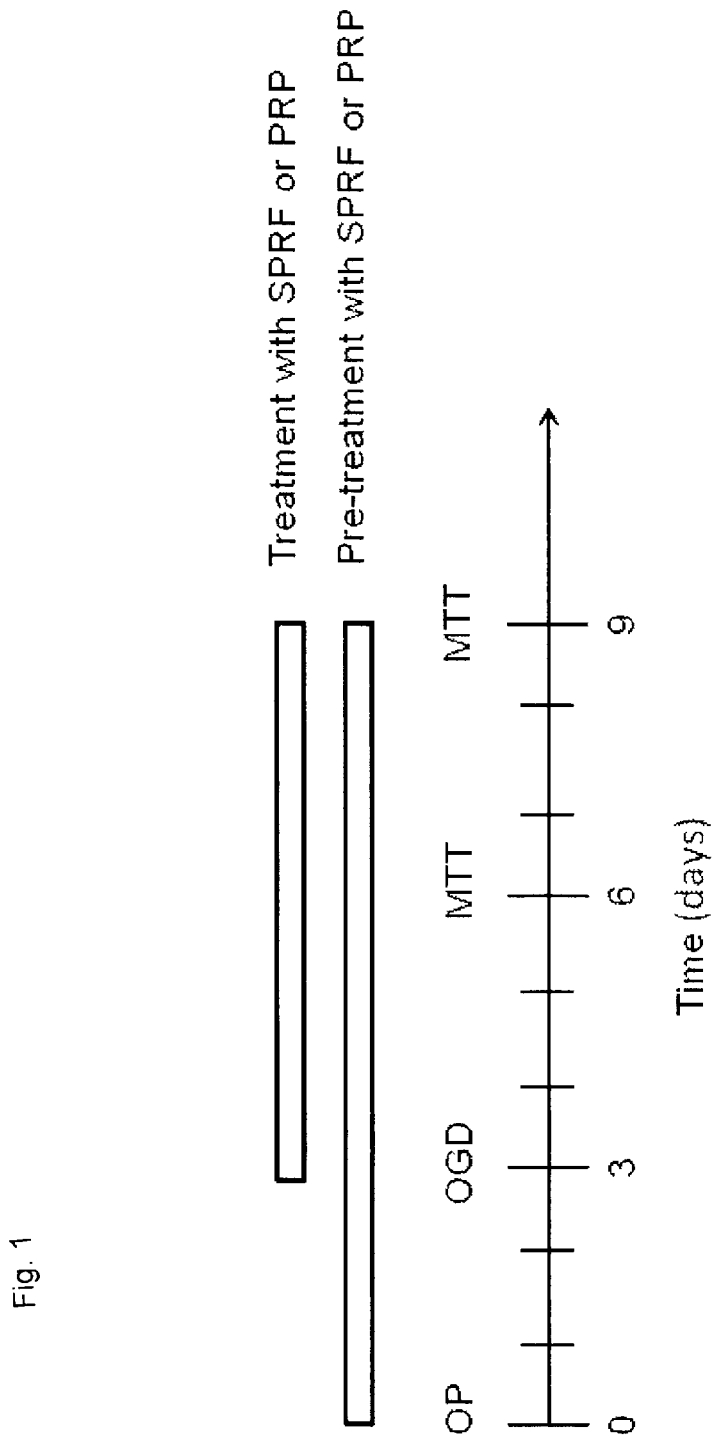

This application is a divisional of U.S. application Ser. No. 14/178,573, filed Feb. 12, 2014, the entire disclosure of which is hereby incorporated by referenced herein. This application claims priority to U.S. Provisional Application No. 61/763,504 filed Feb. 12, 2013.

FIELD OF THE INVENTION

The invention refers to a method of preparing an isolated serum fraction of platelet rich fibrin, and its medical use.

BACKGROUND

Platelets or thrombocytes in mammals are small, irregularly shaped cell-like compartments in blood without a nucleus, which are derived from precursor megakaryocytes. Platelets play a fundamental role in hemostasis. Platelets isolated from peripheral blood are an autologous source of growth factors. In the art various platelet concentrates have been used to accelerate soft-tissue and hard-tissue healing. Platelet concentrates are blood-derived products traditionally used for example to treat consequences of thrombopenia. It has long been recognized that several components in blood a part of the natural healing process and can accelerate healing when added to surgical sites Fibrin glue is formed by polymerizing fibrinogen with thrombin and calcium. It was originally prepared using donor plasma; however, because of the low concentration of fibrinogen in plasma, the stability and quality of fibrin glue were low.

Platelet rich plasma (PRP) in a sense is an autologous modification of fibrin glue, which has been described and used in various applications with apparent clinical success. PRP obtained from autologous blood is used to deliver growth factors in high concentrations to the site of bone defect or a region requiring augmentation. Platelet-rich plasma (PRP) is an easily accessible source of growth factors to support bone- and soft-tissue healing. It is derived by methods that concentrate autologous platelets and is added to surgical wounds or grafts and to other injuries in need of supported or accelerated healing. A blood clot is the center focus of initiating any soft-tissue healing and bone regeneration. In all natural wounds, a blood clot forms and starts the healing process. PRP is a simple strategy to concentrate platelets or enrich natural blood clot, which forms in normal surgical wounds, to initiate a more rapid and complete healing process. A natural blood clot contains 95% red blood cells, 5% platelets, less than 1% white blood cells, and numerous amounts of fibrin strands. A PRP blood clot contains 4% red blood cells, 95% platelets, and 1% white blood cells.

While the use of PRP in bone healing does have a sound scientific basis, its application appears only beneficial when used in combination with osteoconductive scaffolds. Aggressive processing techniques and very high concentrations of PRP may not improve healing outcomes. Moreover, many other variables exist in PRP preparation and use that influence its efficacy; the effect of these variables should be understood when considering PRP as a therapeutic measure.

Platelet-rich fibrin (PRF) belongs to a new generation of platelet concentrates allowing a simplified processing and handling. The slow polymerizing PRF membrane is particularly favorable to support the healing process, however, the biology behind the effect of PRF is still largely unknown and it is only suggested that the effect is due to certain soluble molecules are most likely trapped in fibrin meshes of PRF. PRF is also used in combination with freeze-dried bone allograft to enhance bone regeneration in sinus floor elevation.

Several techniques for platelet concentrates are available and their application may be confusing because each method leads to a different product with different biology and potential uses.

WO2010/089379A1 describes the combination of anticoagulated (soluble) platelet rich plasma (PRP) with a coagulation factor to activate PRP when administering the combination to a patient.

US2009/0047242A1 describes a conditioned blood composition which is prepared by incubating blood in a vessel that has a specific surface area to induce factors and cytokines, such as Interleukin-6.

WO2010/02047A1 describes a blood product comprising fibrin, thrombocytes and leukocytes, which is obtained by surface activation of blood coagulation.

WO2007/127834A2 discloses a thrombin composition obtained by contacting whole blood, a component thereof or fraction thereof with a contact activation agent, such thrombin composition containing a stabilizing agent, such as ethanol.

The terminology of these platelet concentrates, including PRP, PRF, platelet gel, fibrin glue and also platelet poor plasma (PPP) remains uncertain and their effect—despite the several positive results obtained in certain situations, controversial. A general classification is of these products is suggested by Dohan et al (Curr Pharm Biotechnol. 2012 June; 13(7):1131-7.).

Bone ischemia or ischemic bone necrosis (avascular necrosis, osteonecrosis, bone infarction, aseptic necrosis) is a disease wherein cellular death (necrosis) of bone components is due to an interruption of the blood supply of the bone tissue. As a result, the bone tissue dies; this necrosis of cell touches at the first place hematopoietic cells. If the disease affects the bones of a joint, it probably leads to destruction of the joint articular surfaces. Ischemic bone necrosis may be caused e.g. by traumatic injury, fracture or dislocation of the bones, dislocated hip or excessive alcohol consumption or use of steroids.

Upon reperfusion, repair of ischemic bone occurs. At first, mesenchymal cells and macrophages migrate from the living bone tissue grow into the dead bone marrow spaces and then the mesenchymal cells differentiate into osteoblasts and fibroblasts.

Possible treatment includes the replacement of the dead tissue and/or the use of compounds, which may reduce the rate of bone breakdown. There is still a need, however, for materials, which facilitate bone regeneration after the ischemic event.

Recent advances in regenerative medicine shed light on the capabilities of various growth factors, which have remarkable effects as inducers of bone formation. In addition to bone morphogenic proteins, platelet-derived growth factor (PDGF), transforming growth factor beta (TGF-beta), insulin-like growth factor (IGF) and epidermal growth factor (EGF) also have a positive effect on bone regeneration. Single factor therapies are available as recombinant products, currently BMP-2, -7, and PDGF have marketing approval, or as natural extracts typically isolated from venous blood.

Positive effects of PRP in dental tissue repair and in other maxillofacial cases are widely practiced. PRP is also applied for the treatment of other pathologies such as osteoarthritis, tendinitis and nerve injury and is gaining traction as a 'cure-all' for many musculoskeletal diseases. However, the exact mode of action is unknown and the general perception of PRP is that both the protocols and the results are highly variable.

SUMMARY OF THE INVENTION

It is an object of the invention to provide for an improved blood preparation, in particular to support repairing bone ischemic events.

The object is solved by the subject of the inventions disclosed herein.

According to the invention there is provided a method of preparing an isolated serum fraction of platelet rich fibrin (PRF), comprising the steps of
   a. providing platelet rich plasma (PRP) without the addition of an anticoagulant;
   b. clotting the PRP to obtain a coagel of PRF; and
   c. separating the coagel to isolate the serum fraction which comprises an activated platelet releasate.

Specifically, method steps a. and b. may be carried out in a single step procedure, e.g. wherein PRP is produced from a blood sample by fractionation during which the coagel is formed, e.g. by active activation of coagulation or self-activation of coagulation. More specifically, method steps a., b. and c. may be carried out in a single step procedure, e.g., in a closed system.

Specifically, the PRP is prepared by separating the red blood cell fraction from a venous blood sample, preferably wherein the PRP is clotted during its preparation.

Specifically, the PRP is employed without exogenous anticoagulants that are commonly used when preparing PRP, thereby an effective activation of platelets and a content of an activated platelet releasate in the isolated serum fraction is obtained according to the invention.

Specifically, the PRP is clotting spontaneously during its preparation by centrifuging a blood sample, preferably accelerated upon contact with negatively charged surfaces and without adding exogenous coagulation activators.

In the prior art, the PRP was typically produced as anticoagulated preparation, e.g. from blood or PRP collected with anticoagulants, such as heparin, citrate, acid citrate dextrose (ACD) and citrate-theophylline-adenosine-dipyridamole (CTAD). Such anticoagulants were known to preserve the platelets maintaining the integrity of platelet structures. In contrast, the present invention is based on the PRP plasma activation which PRP does not contain such anticoagulants, supporting the effective production of invaluable growth factors and cytokines which are released by the platelets activated according to the method of the present invention.

Specifically, the coagel is separated by pressing, squeezing, filtering and/or centrifuging the coagel to isolate the serum fraction containing the fluid fraction of PRF.

The serum fraction of the invention, hereinafter also referred to as SPRF (serum of PRF), may include the supernatant of the coagel e.g. obtainable by centrifugation, and/or the fluid fraction obtained from the coagel, e.g. SPRF which essentially consists of the fluid fraction. For example, such serum fraction essentially consisting of the PRF fluid fraction is prepared upon fractionating the PRF to isolate the fluid fraction from PRF, e.g. by separating the solid coagel mainly consisting of fibrin gel and platelets. Specifically, upon clotting the PRP and formation of the PRF, the acellular or clear supernatant from the PRF may be isolated, or may be removed before fractionating the PRF to isolate the PRF fluid fraction. Such PRF fluid fraction turned out to contain the highest concentration of activated platelet releasate and growth factors contained therein.

Specifically, the PRP may be obtained from a blood sample from a single donor or from multiple donors and mixed together to obtain a single blood sample. According to a specific aspect, the PRP is obtained from venous blood collected from a single donor.

The blood sample can further be obtained from the same individual who will receive the serum fraction. Thus, the blood and serum fraction can be autologous to the recipient. Specifically, autologous venous blood or PRP may be used.

The blood sample can also be obtained from a non-autologous individual or donor or multiple donors. Moreover, the blood sample can be obtained from a heterologous individual or donor or multiple donors. Thus, the blood sample can be obtained from one or more individuals. The serum fraction of the invention which is heterologous may specifically be treated to inactivate or remove possibly present blood borne viruses by conventional virus inactivation or depletion methods, including treatment with solvent and detergent, low pH and/or nanofiltration. Alternatively and/or additionally, the virus safety may be ensured by selecting suitable donors which have been determined not to be infected with blood borne pathogens.

Typically, the volume of such blood sample is ranging between 1 ml to 100 ml, preferably between 10 ml to 40 ml more preferably between 15 ml to 35 ml.

According to a specific aspect, the blood sample is collected in a clot device such as a clot tube or clot syringe, optionally wherein the PRP is prepared and clotted to obtain the coagel, e.g. a clot activating tube or syringe, which is typically equipped with appropriate coagulation initiators or accelerators, herein referred to as "coagulation activators". For example, typical clot tubes may provide for a negatively charged contact surface, such as glass, which would accelerate spontaneous clotting of the PRP during separation of the red blood cell fraction.

The device may not only be used for collecting the blood, but also for preparing the PRP, e.g. by centrifugation of the blood sample in one or more consecutive steps.

The device may also be suitable for separating specific blood products besides the physico-chemical separation by e.g. filtration or allocating specific blood separation fractions to another chamber or barrel of the device. Optionally, the PRP is prepared and clotted in or by means of such device to obtain the coagel.

Specifically preferred contact activators are anorganic, physical and/or biologic contact activators. According to a specific aspect, coagulation is accelerated or activated through the contact activation pathway, specifically upon contact with negatively charged surfaces, preferably glass e.g. silicate, borosilicate; kalomel, diatomaceous earth polymers with a polar structure, e.g. acrylates, carbonates, or polyacrylamides, specifically those which are physical contact activators.

Alternative activators may be biological or chemicals like collagen, CaCl2, Ca-gluconate, MgCl2, thromboxane A2, ADP, thrombin, D-glucose, dextran, glycerol. These activators may be present as a coating, bead, or porous sponge. The activator may also be an enzyme or amino acid, like thrombin, thromboplastin or coagulation factors e.g. FIIa, FXa, FVIIa, FIXa, FXIa, FXIIa, FXIVa.

According to specific embodiments, it is preferred to prepare the serum fraction by endogenous clotting of the PRP, i.e. by physical contact with suitable surfaces only, thereby avoiding exogenous additives which would possibly contaminate the serum preparation. Such endogenous clotting would provide for the endogenously activated platelets, allowing the collection and isolation of the fluid fraction of PRF or the serum fraction of the invention containing the activated platelet releasate obtained from such activated platelets without exogenous contaminants. Specifically, in such embodiment the addition of exogenous thrombin or other coagulation factors is avoided.

According to a specific aspect, the serum fraction is freshly prepared without adding preservatives, such as ethanol, and e.g. prepared without any intermediate storage or freezing/thawing step. Typically, the preparation method would be carried out during a short period of time to obtain a freshly prepared serum fraction, e.g. a period up to 10 hours, specifically less than 6 hours.

Such serum fraction is e.g. prepared ready-to-use for the purpose of treating a patient without using a preservative. Thus, stabilizing agents, such as high concentrations of alcohol or further preservatives are avoided. Yet, the freshly prepared serum fraction is storage stable at lower temperatures and may be stored at refrigerating temperatures or frozen over a longer period of time, e.g. at 2° C.-12° C. for up to 1-24 months, or at −80° C. to −25° C. for up to 0-5 years.

For example, a serum fraction of the invention, e.g. an autologous preparation, may be freshly prepared employing bedside methods to collect blood from individual patients, followed by concentration and activation of platelets through coagulation activation.

According to a specific example, the clotting or coagulation activation, herein also called "activation of PRP" is effected by an incubation step during which the coagel is formed, e.g. where the PRP is allowed to stand at room temperature up to 37° C., preferably about 18-25° C., for about 1-8 h, preferably for about 2-6 h.

According to a specific aspect, the serum fraction comprises a platelet releasate from activated platelets.

According to a specific aspect, the platelet releasate is enriched in platelet factors released from the activated platelets as compared to PRP. Among the platelet factors there is specifically a series of growth factors, cytokines, interleukins, chemokines, and angiogenesis or growth factor related proteins.

Preferably, the serum fraction contains specific factors, and is typically characterized by a specific profile of such factors, among them growth factors and cytokines. For example, the serum fraction contains at least one of angiogenesis or growth factor proteins selected from the group consisting of Activin-A, ADAMTS-1, Angiogenin, CXCL16, DPPIV, Endoglin, Endostatin/Collagen XVII, FGF-4, GM-CSF, HB-EGF, HGF, IGFBP-1, IGFBP-2, IGFBP-3, IL-1β, IL-8, LAP (TGFβ-1), Leptin, MCP-1, MMP-8, MMP-9, NRG1-β1, Pentraxin-3, PD-ECGF, PDGF-AB/PDGF-BB, PlGF, Prolactin, TIMP-4, Thrombospondin-1, uPA, e.g. at a similar (such as 10%, 15%, or less than 20% difference) or different level (such as a change of at least 20%) compared to PRP or whole blood, e.g. measured by a proteome profiler array, ELISA or similar assays. Specifically, at least 2 of these factors are present, or at least 3, 4, 5, 6, 7, 8, 9, or 10, or even more, at least 15, 20, 25 or up to all of these factors are present.

Specifically, one or more of these factors are enriched in the serum fraction of the invention. The enrichment of the specific factors is typically determined, if the concentration is increased by at least 20%, 30%, 40% or 50%, or even at least 100%, or at least 2-fold, at least 3-fold, or at least 4-fold increased, as compared to PRP or whole blood.

Specifically, the serum fraction is enriched in at least one of angiogenesis or growth factor related proteins selected from the group consisting of Platelet factor 4, Serpin E1, or TIMP-1, as compared to PRP or whole blood, e.g. measured by a proteome profiler array, ELISA or similar assays. Specifically, the serum fraction is enriched in one, two, or all three of these selected factors.

According to a further specific embodiment, the serum fraction is specifically characterized by an increased Platelet factor 4 concentration as compared to PRP or whole blood, e.g. at least 2-fold, preferably at least 3-fold, at least 4-fold or 5-fold enriched measured by a proteome profiler, ELISA or similar assays.

Specifically, one or more of these factors are depleted in the serum fraction of the invention, i.e. the content or concentration reduced. Specifically, the serum fraction is depleted in at least one of angiogenesis or growth factor related proteins selected from the group consisting of SDF-1, Angiopoietin-1, EGF, PDGF, VEGF, as compared to PRP or whole blood, e.g. measured by a proteome profiler array, ELISA or similar assays.

According to a specific embodiment, the serum fraction is characterized by a decreased concentration of stromal cell-derived factor 1 (SDF-1, CXCL12) as compared to PRP or whole blood. Specifically, the SDF-1 concentration measured is less than 350 pg/ml, preferably less than 275 pg/ml measured by ELISA.

According to a further specific embodiment, the serum fraction is characterized by a decreased Angiopoietin-1 concentration as compared to PRP or whole blood.

According to a further specific embodiment, the serum fraction is characterized by a decreased Epidermal Growth Factor (EGF) concentration as compared to PRP or whole blood.

According to a further specific embodiment, the serum fraction is characterized by a decreased Platelet derived growth factor (PDGF) concentration as compared to PRP or whole blood.

According to a further specific embodiment, the serum fraction is characterized by a decreased Vascular Endothelial Growth Factor (VEGF) concentration as compared to PRP or whole blood.

Specifically, the serum fraction is characterized by the depletion or reduction of two, three, four, or all five of these depleted factors, e.g. wherein one of these is at least SDF-1 or whole blood.

The depletion, i.e. decrease or reduction of the specific factors is typically determined, if the content or concentration is less than 50%, or less than 40%, or less than 30%, or less than 20%, or less than 10%, or less than 5% (w/w) of the concentration or content as compared to PRP or whole blood, e.g. measured by a proteome profiler, ELISA or similar assays.

Specifically, the serum fraction is depleted or free of red blood cells, e.g. substantially lacking red blood cells such that more than 75%, preferably more than 95% are removed, as compared to whole blood.

According to a specific embodiment, the serum fraction is further characterized by a reduced content of platelets as compared to whole blood, e.g. 10-fold, preferably 20-fold reduced. Upon separation of the coagel, the serum fraction typically contains less than 50*109/l platelets, preferably less than 10*109/l.

According to a specific embodiment, the serum fraction is further characterized by a reduced content of fibrinogen (e.g. determined by the fibrinogen plus fibrin content) as compared to whole blood, e.g. less than 20%, or less than 10%, or less than 5% (w/w). Upon separation of the coagel, the serum fraction typically contains less than 1.5 g/L fibrinogen+fibrin, preferably less than 0.5 g/L. Typically, the serum fraction is a clear or opaque solution without solid mass, e.g. without a fibrin clot visible to the naked eye.

According to a specific aspect, the serum fraction is freshly prepared and ready-to-use, optionally wherein the serum fraction is provided in an application device, specifically a syringe. Specific embodiments refer to an autologous serum fraction, i.e. a serum fraction prepared from blood or PRP of a single individual donor, which is read-to-use for administration to the same individual. The serum fraction may be conveniently prepared in an appropriate preparation device suitable for aseptic collection of the blood, preparing the PRP, clotting the PRP (e.g. by actively initiating coagulation or by self-activation), separating the coagel and optionally further separating the solid PRF to isolate the serum fraction with or without the PRF fluid fraction, or to isolate the serum fraction from the PRF coagel. Specifically, the preparation device is suitable for aseptic collection of the blood, and preparing the PRP while it is self-activated whereupon a coagel is formed, and further separating the PRF coagel and obtaining the coagel supernatant together with the fluid fraction of the PRF.

The isolated serum fraction may be produced in the application device in an aseptic way and may conveniently be directly and immediately administered to the individual, e.g. by an applicator aseptically connected to the preparation device, or by a separate application device or kit which allows the aseptic transfer of the prepared serum fraction to the application device and/or to administer the preparation to the individual.

According to the invention, the serum fraction is specifically provided for use in the manufacturing of an autologous pharmaceutical or medicinal product. Such product may be in the form of a pharmaceutical preparation or a medical device preparation.

Specifically, the serum fraction is provided for the treatment of the serum fraction's donor. Specifically, the autologous use of the serum fraction is preferred.

Specifically, the invention provides for the medicinal use, e.g. for plastic, reconstructive or regenerative medicinal use, specifically for use in orthopedic, surgical and/or cosmetic treatment.

Specifically, the serum fraction is used for treating a patient suffering from osteonecrosis, e.g. femoral head, Köhler I and II, Perthes, Schlatter-Osgood, or Scheuermann, osteoarthritis, osteoarthrosis, bone necrosis, tendinosis, e.g. tennis elbow, plantar fasciitis, or jumper's knee, critical limb ischemia, Buerger's disease, impingement syndrome, e.g. of the shoulder or the hip, or a patient undergoing treatment for dermal filling, rejuvenation of the nasolabial crest or any other facial wrinkles, bone grafting or implantation.

The serum fraction of the invention would specifically induce proliferation after ischemia on explants of human osteonecrotic material. Specifically, when the serum fraction is mixed with bone grafts in vitro or in situ, the regeneration of bone material could be determined.

Specifically, the invention provides for the use of the autologous serum fraction, e.g. collecting a blood sample from a patient who is suffering in or having suffered in a disorder or disease condition, and to whom the preparation is administered to.

In general terms, the invention specifically provides for the serum fraction of the invention for medical use. Accordingly, the invention further refers to a method of treating a patient in need thereof with an effective amount of the serum fraction. Such effective amount is typically an amount sufficient to treat, repair or augment cells or tissue, e.g. local or topical treatment at a target site in need of cell proliferation or regeneration, e.g. skin, a wound, an injury, an incision, or a surgical site.

Specifically, the serum fraction is provided for use in the treatment of a patient suffering in or having suffered in bone ischemia or a related bone disease, including bone necrosis, osteoarthrosis or osteoarthritis, or other degenerative bone disease. Specifically, the serum fraction is provided for use in facilitating or accelerating the propagation of bone tissue cells and thereby bone tissue regeneration after bone ischemia, or for use in the treatment of bone ischemia or any related disease or a disease which is a consequence of bone ischemia or a disease mediated by bone ischemia.

Accordingly, the invention further provides for a method for the treatment of a patient suffering in or having suffered in osteoarthritis, osteoarthrosis, bone necrosis, bone ischemia, or a disease as defined herein, comprising the steps of administering a serum fraction of the invention to said patient.

Specifically, the invention provides for a method for facilitating or promoting the propagation of bone tissue cells and thereby bone tissue regeneration comprising the steps of administering the serum fraction of the invention to a bone tissue under or having subjected to bone ischemia, optionally to a patient suffering in or having suffered in osteoarthritis, osteoarthrosis, bone necrosis or bone ischemia.

According to the invention, there is further provided a method of promoting in vitro proliferation of cells by contacting a serum fraction of the invention with said cells and incubating said cells for a period of time sufficient to promote cell growth or regeneration, specifically wherein the cells are epithelial cells, stem cells or bone cells, e.g. osteocytes, osteoclasts, osteoblasts, or bone marrow derived cells such as mesenchymal stem cells and progenitor cells derived from them. Such in vitro treatment is specifically useful for preparing autogenous bone material or allografts.

Specifically, the serum fraction is provided for in vitro use as a cell culture additive or to prepare bones or implants, e.g. metal implants, specifically by surface treatment or coating. For example, the serum fraction is used in preparing dental bone grafts support.

Specific treatment methods according to the invention— either in vitro or in vivo—would refer to restoring the proliferation capacity of post-ischemic bone, effectively promoting vascularization and/or angiogenesis in regenerating tissue, or promoting the migration and/or infiltration of endogenous wound healing component such as include periosteogeneic cells, angiogenic cells, stromal cells, mesenchymal cells, osteoprogenitor cells, osteoblasts, osteoclasts, or platelets. Specific treatment methods refer to bone, periosteum, tendon, muscle, fascia, nerve tissue, vascular tissue, and combinations thereof.

According to the invention there is further provided a pharmaceutical preparation comprising the serum fraction and a pharmaceutically acceptable carrier.

Specifically, the pharmaceutical preparation further comprises an additional active substance and/or device to promote wound healing, cell proliferation or regeneration.

Specifically, the additional active substance is a hydrogel, a tissue sealant or an active component thereof, e.g. a gellifying agent which forms a hydrogel upon contact with the serum fraction of the invention, a tissue sealant component comprising fibrinogen and/or collagen, and/or a tissue sealant component comprising thrombin or prothrombin in combination with a prothrombin activator to generate thrombin. Specifically, the device is a solid or semi-solid or gel-like biomaterial suitable for use in humans (resorbable or non-resorbable), e.g. a bone graft material, e.g. including autogenous bone material, allografts, such as demineralized freeze-dried bone material, or alloplasts such as hydroxyapatite and tricalcium phosphate of synthetic or natural origin.

Specifically, the pharmaceutical preparation is provided ready-to-use, e.g. contained in an application device, in particular a syringe.

According to the invention, there is further provided an application kit comprising the components
  a. the serum fraction of the invention; and
  b. an application device, specifically a syringe.

Specifically, the kit may include further components or combinations, e.g. as a further component
  c. a bone graft material, a gelling agent, a tissue sealant or an active component thereof; and
  d. optionally a device for mixing the components a. and c. to obtain a mixture ready for application.

FIGURES

FIG. 1. Protocol of simulated ischemia and reperfusion in human bone explants. Bone tissue pieces were isolated at day 0 at total hip replacement procedures and kept in culture for 3 days. Cells were subjected to damage through oxygen glucose deprivation (OGD) for 7 hours on day 3, followed by the replacement of normal stem cell medium and a return of oxygen levels to normal. Serum fractions were added to the explanted cultures at just before OGD and replaced at medium changes when necessary until the end of the experiment. Cell viability was measured on either the 6th or the 9th days by replacing the tissues in a fresh well and thus measuring the cells on the bone matrix only.

Figure 2:
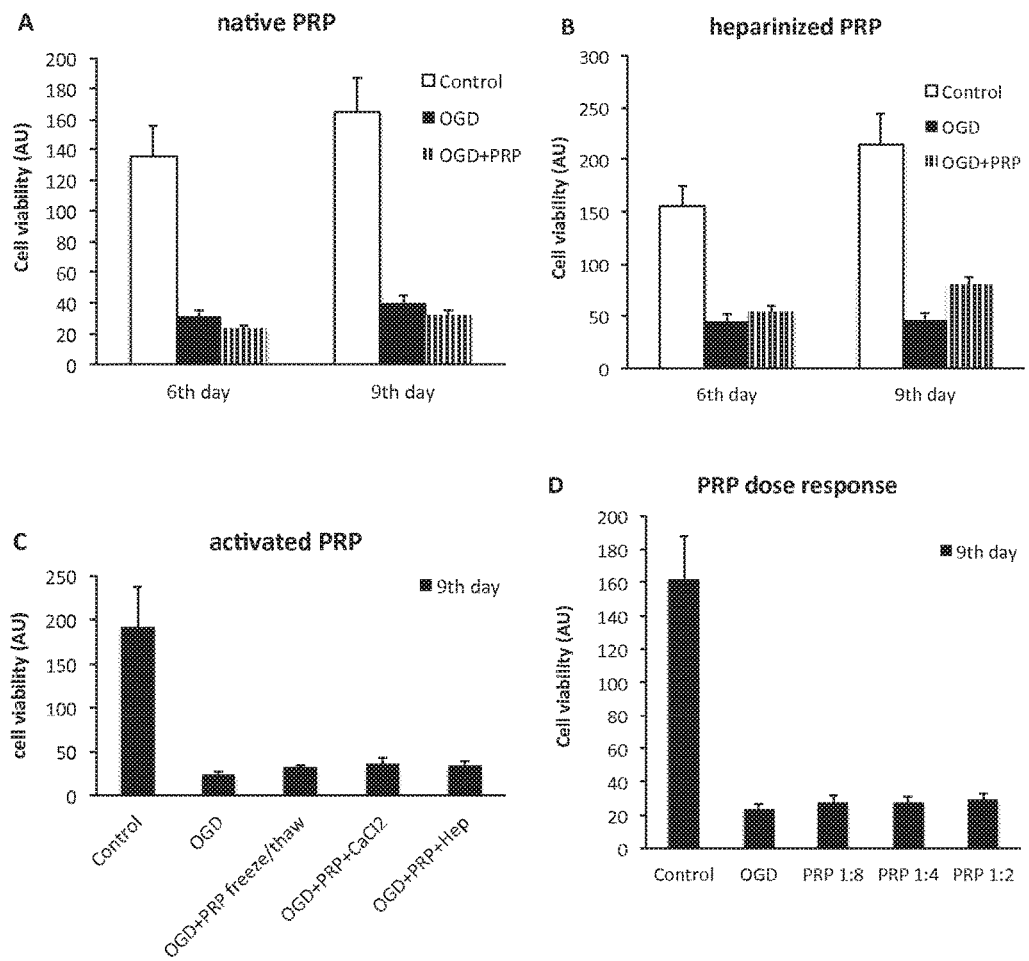

FIG. 2. Effect of PRP treatment on bone explants after OGD. Panels A and B show that neither PRP nor heparinized PRP has any effect on cell viability after 3 or 6 days reperfusion (n=24/group). Panel C shows that increasing the concentration of PRP to the technically feasibly maximum level without affecting the native preparation has still no effect on the proliferation. PRP activated by different ways such as adding Calcium, Calcium+Thrombin, or subjecting the preparation to 3 cycles of freezing and thawing was also without effect (Panel D). Data are presented as average±SEM.

Figure 3:
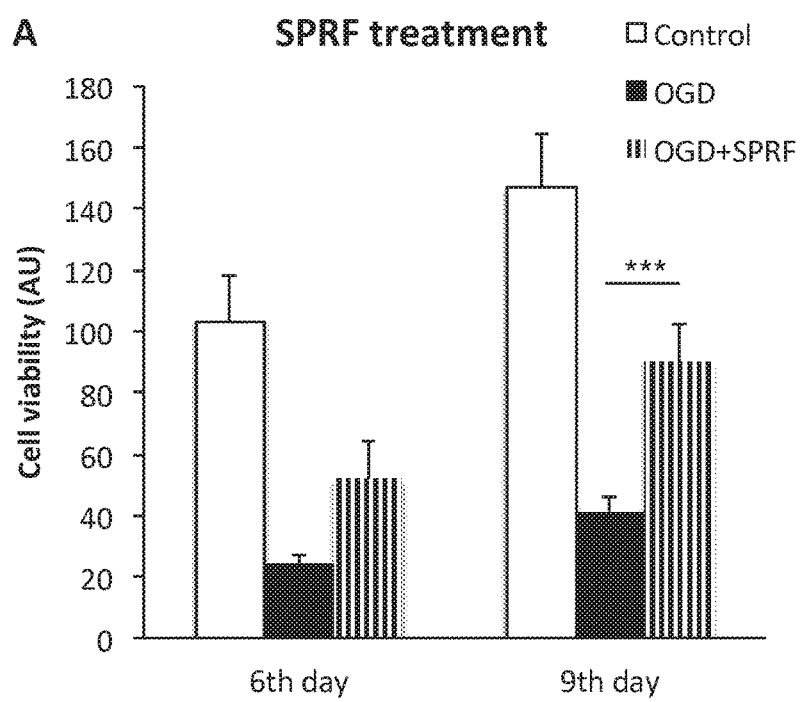
Figure 3:
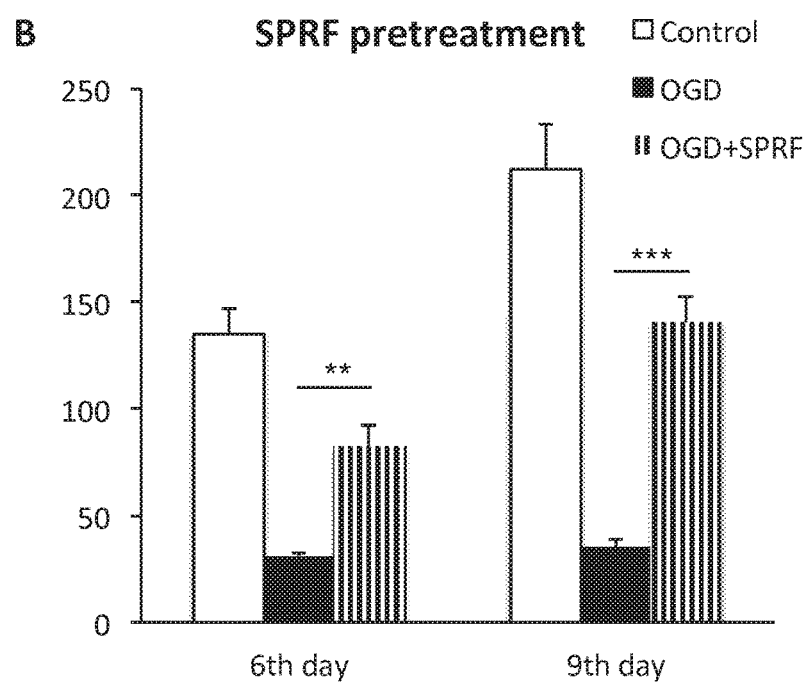

FIG. 3. Effect of SPRF on bone explants after OGD. Panel A shows that there is no effect immediately after 7-hours OGD (n=18-24/group), but cells started to proliferate significantly better after 6 days. Panel B shows the effect of SPRF-pretreatment when the serum fraction was present in the medium from day 0 (n=24/group). Data are presented as average±SEM,  represents p<0.01, * represents p<0.001.

Figure 4:
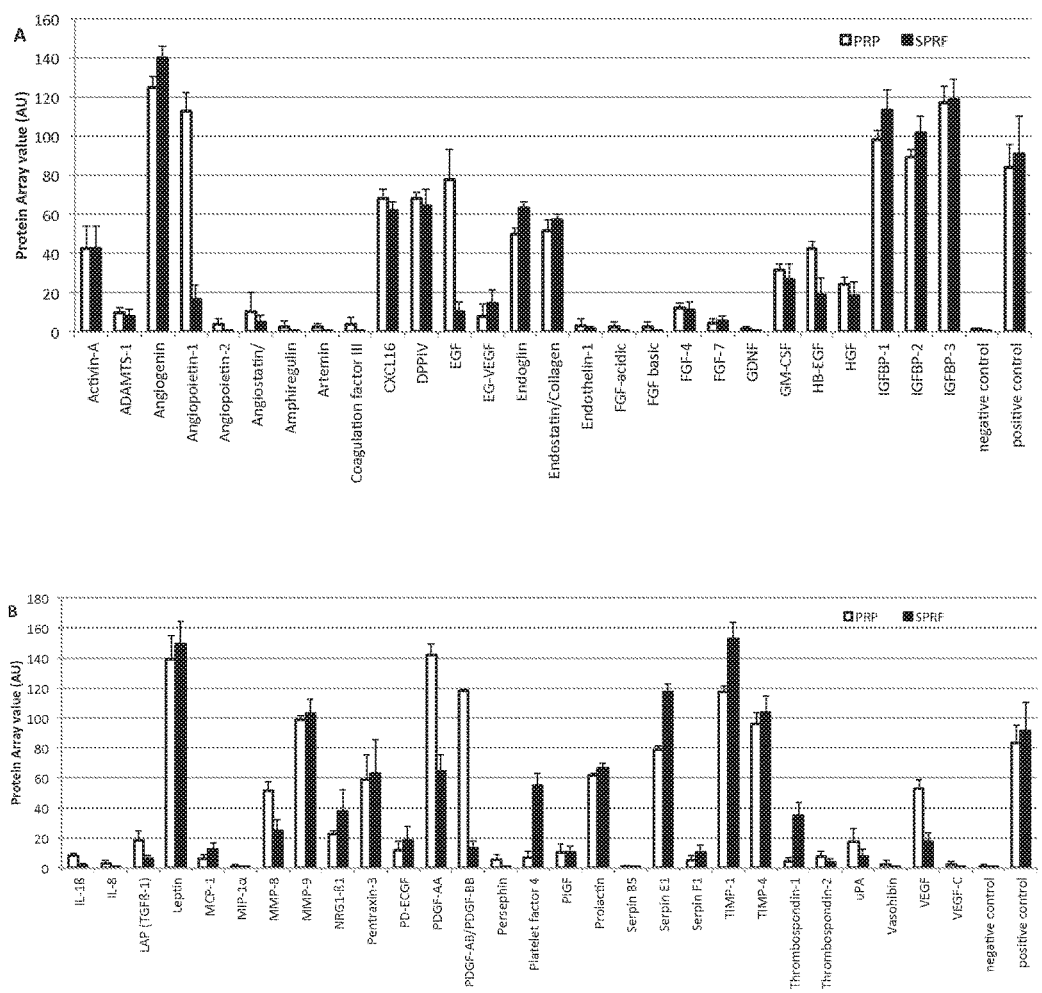

FIG. 4. Constituents of serum fractions measured by the ProteomeProfiler array. Protein levels are measured by the intensity of spots in arbitrary units, compared between SPRF and PRP. Data are split between panels A and B for legibility. Data are presented as average±SEM, n=3 subjects, each spot is measured in duplicates.

DETAILED DESCRIPTION

The term "clotting" as used herein in relation to blood coagulation is herein understood in the following way. Platelet activation and subsequent degranulation and aggregation play a pivotal role in blood clotting. Coagulation can be activated through the intrinsic or "contact activation pathway" which is initiated when blood coagulation factor XII comes into contact with negatively charged surfaces in a reaction involving high molecular weight kininogen and plasma kallikrein. FXII can be activated by so-called "contact activators", e.g. the biological macromolecular constituents of the subendothelial matrix such as glycosaminoglycans and collagens, sulfatides, nucleotides, and other soluble polyanions or non-physiological material such as glass, or polymers, in particular artificial negatively charges surfaces, such as glass beads. Besides, the coagulation cascade supports the blood coagulation process. The coagulation cascade involves a series, i.e. cascade of reactions, in which a zymogen is activated, e.g. by enzymes supported by co-factors, to become an active enzyme that then catalyzes the next reaction in the reaction cascade, ultimately resulting in the formation of a fibrin clot, which strengthens the platelet aggregate. The zymogens are also known as coagulation factors or clotting factors.

As a result of coagulation activation, a blood clot is formed, which is herein referred to as a "coagel". A coagel is specifically understood as the coagulated phase of blood, i.e. the soft, coherent, jelly-like mass resulting from the conversion of fibrinogen to fibrin mainly consisting of fibrin fibers associated to form a fibrin gel or clot. The coagel as described herein specifically is entrapping platelets and further components of coagulated plasma.

The coagel emanated from PRP is specifically understood as platelet rich fibrin (PRF) which may specifically include aggregated fibrin and blood cells, such as platelets, white blood cells, and/or red blood cells.

The coagel of PRF is herein understood to be composed of two fractions, the fluid fraction and the solid fraction, which may be physically separated to isolate the liquid phase and discard the solid mass.

Coagulation is specifically activated in a suitable container, such as a clot container or clot activating container, e.g. a tube. The container is suitably a glass or plastic container, with or without additional means to initiate or accelerate clotting, e.g. blood collection tubes generally used in the medical practice.

In particular, the clot container does not contain anticoagulants, and is used without adding anticoagulants, so to support the clotting in situ. According to a specific embodiment, the clot container is suitably equipped with contact activating surfaces to activate the intrinsic coagulation pathway.

The term "platelet rich plasma" or PRP is herein understood as a volume of plasma that has a platelet concentration above baseline. Normal platelet counts in blood range between 150,000/microliter and 350,000/microliter. The platelet concentration is specifically increased by centrifugation, and/or otherwise fractionation or separation of the red blood cell fraction, e.g. centrifugation of whole blood first by a soft spin such as 8 min at 460 g and the buffy coat is used or further pelleted by a hard spin at higher g values. PRP typically comprises an increased platelet concentration, which is about a 1.5-20 fold increase as compared to venous blood.

Such centrifugation and/or fractionation will separate the red blood cells from blood, and further separate the platelet rich fraction (PRP) including platelets, with or without white blood cells together with a few red blood cells from the platelet poor plasma. PRP may be further concentrated by ultrafiltration, where the protein content of the platelet-rich plasma is concentrated from about 5% to about 20%.

PRP may be activated by the method as described herein, in particular by clotting, which specifically activates the platelets contained in PRP in the absence of exogenous anticoagulant additives. The present invention specifically provides for activation of PRP, e.g. such that the majority of the platelets are activated. Thus, at least 50% of the platelets in the PRP are activated though the activation of coagulation.

The term "administration" as used herein shall include routes of introducing or applying activated a preparation, such as the serum fraction of the invention, to a subject in need thereof to perform their intended function.

Preferred routes of administration are local, including topical or mucosal application, or application to a wound site or a site of (surgical) intervention, such as by using a fluid, spray, hydrogel, cream or ointment, or else by any other convenient route, including systemic administration, for example, injections, such as by subcutaneous, or intra-articular injections, by injecting into the layers of skin, under the skin into the epidermis, into fat pads muscles of various soft tissues, into cancellous bone and bone marrow, sprayed onto tissue surfaces, mixed with bodily fluids, etc.

Various known delivery systems, including syringes, needles, tubing, bags, etc., can be used. Specific delivery systems employ patches for topical delivery, or implants. Specifically preferred are slow-release preparations, e.g. in the form of a hydrogel, a semisolid or solid gel or formulations and delivery systems to provide for the long-acting treatment.

The serum fraction can be administered alone, or in combination or conjunction with either another agent or any other therapeutic treatment used in the indication, e.g. used to treat patients suffering from osteoarthritis, osteoarthrosis, bone necrosis, or bone ischemia. The serum fraction can be administered prior to the administration of the other agent, simultaneously with the agent, or after the administration of the agent. An alternative delivery system provide for the serum fraction associated with or bound to a carrier material, e.g. a gel or an implant.

The term "isolated" as used herein with respect to a serum fraction shall refer to such fraction of blood, plasma or serum that has been sufficiently separated from other fractions or blood components with which it would naturally be associated. In particular, the serum fraction of the invention is isolated so as to be separated from the PRF coagel and/or from the solid fraction of the PRF coagel. "Isolated" does not necessarily mean the exclusion of artificial or synthetic mixtures with other fractions, compounds or materials, or the presence of impurities that do not interfere with the fundamental activity. In particular, active substances and surgical materials may be combined with the isolated serum fraction of the invention.

The term "pharmaceutically acceptable carrier" as used herein shall specifically refer to any and all suitable solvents, dispersion media, coatings, antibacterial and antifungal agents, isotonic and absorption delaying agents, and the like that are physiologically compatible with a serum fraction provided by the invention. Further examples of pharmaceutically acceptable carriers include sterile water, saline, phosphate buffered saline, dextrose, glycerol, ethanol, and the like, as well as combinations of any thereof. In one such aspect, a serum fraction can be combined with one or more carriers appropriate a desired route of administration. Such carriers and modes of administration are well known in the pharmaceutical arts. A carrier may include a gel or hydrogel, or gellifying agent or gelling agent, controlled release material or time delay material, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, gelling and chelating agents. Exemplary formulations may be provided, e.g. as a hydrogel including more than 50% water by weight.

In one embodiment, the serum fraction of the present invention is the only therapeutically active agent administered to a subject, e.g. as a disease modifying or preventing monotherapy.

In another embodiment, the serum fraction of the present invention is combined with further active agents or materials e.g. combined in a mixture or kit of parts. The serum fraction of the present invention may be administered in combination with one or more other therapeutic or prophylactic active agents or regimens, including but not limited to standard treatment, e.g. antibiotics, steroid and non-steroid inhibitors of inflammation, anti-inflammatory agents, vitamins, or minerals.

The term "subject" or "individual" as used herein shall refer to a warm-blooded mammalian, particularly a human being. In particular, the medical use of the invention or the respective method of treatment applies to a subject in need of prophylaxis or treatment of a disorder or disease condition, e.g. associated with damaged tissue, a wound, an injury, a burn, an incision or an ischemic event, such as osteoarthritis, osteoarthrosis, bone necrosis or bone ischemia, or suffering from such disease condition. The term "patient" includes human and other mammalian subjects that receive either prophylactic or therapeutic treatment. The term "treatment" is thus meant to include both prophylactic and therapeutic treatment, in particular to treat, repair or augment a tissue at a target site.

The biological properties of the serum fraction or the respective pharmaceutical preparations of the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. The serum fraction and respective pharmaceutical compositions of the present invention may further be tested in humans to determine their therapeutic or prophylactic efficacy, toxicity, immunogenicity, pharmacokinetics, and/or other clinical properties.

Further ex vivo or in vivo methods of treatment of cells are envisaged which comprise a cell culture and an incubation step, e.g. in solution or on a solid support, e.g. an implant or bone graft material. Such cell culture or treatment is specifically performed in the following way: Cells are cultured under regular cell culture conditions and the serum fraction of the invention is added to the medium. The addition of the serum fraction specifically induces cell proliferation, prevents cell death or damage and may induce differentiation in specific cell types. Cell proliferation is typically measured by cell counting or surrogate methods.

It was unexpectedly found that certain blood derived preparations accelerate and improve cell proliferation, regeneration and healing of tissue, in particular osteoarthritic material or the bone tissue after ischemic bone damage.

Blood cells, upon activation by injury secrete a plethora of proliferation factors into the serum. This raises the possibility of using serum products for therapeutic targets other than acute injury thus applying a more physiological growth factor mix than the monotherapy of recombinant proteins. Investigations of PRP and related serum fractions in an ex-vivo model of bone ischemia were made. Small bone pieces of 10 mm3 were isolated from the discarded femoral heads during hip replacement operations. The explants were grown in culture for 3 days then subjected to transient oxygen glucose deprivation (OGD) for simulating ischemia. The majority of the cells on the bone explants died and the survivors did not proliferate. Adding PRP that is either native or anticoagulated (heparinized) or activated by chemical or physical means, did not have any effect on the postischemic cells. However, the serum fraction of the invention, in particular containing the fluid fraction of the coagel of PRF, in pancular the serum pressed from platelet rich fibrin (SPRF), induced cell proliferation of the postischemic osteoblasts. Proteome-profiler analysis showed that PRP and SPRF have diverging growth factor profiles, with platelet factor 4 being a key one which has a higher concentration in SPRF than PRP. Another significant difference is the lack of fibrin or fibrinogen in SPRF because clotting is spontaneous and the PRP activated instantly after drawing blood. It is concluded that the serum fraction of the invention, in particular the SPRF, is a blood derivative which can restore the cell proliferation capacities, e.g. of postischemic bone and thus can be a new therapeutic tool, with a specific use in degenerative bone diseases.

The serum fraction of the invention is specifically provided for treating osteoarthritis, osteoarthrosis, bone necrosis or bone ischemia, for implants or autologous bone grafts to prevent or treat ischemia after implantation, or to increase proliferation of cells after an ischemic episode.

Bone ischemia or avascular necrosis (AVN) for example of the femoral head still presents a challenge for the orthopedic surgeons, mainly for the progressive characters of the disease and the relative young age of the patients. Presently available specific and efficient treatments are:
- core decompression
- core decompression
- autologous bone
- demineralized bone-matrix
- BMP (Bone morphogenic proteins)
- osteotomia
- application of promising agents of human blood, e.g. PRP
- any combination of the foregoing.

A human in vitro model was set-up and the effects of blood plasma derived preparations in the pathomechanism of bone ischemia were tested.

Experiments with various plasma fractions were carried out and it was surprisingly found that preparations can be obtained which are effective for accelerating and facilitating bone regeneration after bone ischemia.

The ex vivo results showed that the serum derived preparation of the invention directly induces proliferation of bone cells even after severe ischemia. Proliferation of cells has been found to be significantly improved by either the fluid fraction of PRF, which comprises or consists of the liquid content in PRF, but not by PRP of the prior art.

The experimental results were surprising in view of the prior art. It was specifically surprising that the starting material, which is PRP without the addition of anticoagulants, and the clotting according to the invention affects the final result. Specifically, the freshly prepared serum fraction of the invention could be provided as an improved material for medical use.

Activated fibrin has a strong pro-inflammatory effect which is beneficial in case of acute injuries but may be harmful in chronic cases where regeneration of the tissues is inhibited by persistent inflammation. Therefore, matching the right kind of proliferation factor mix with a certain pathology is necessary in order to develop a reliable clinical protocol. In the present study a novel ex vivo human model of bone ischemia was used, which closely resembles the tissue states of transplanted bone or tissue damaged by end-stage degenerative diseases. The constituents of various platelet-rich serum fractions were analyzed and their effects as proliferation factors on postischemic human bone explants investigated, to confirm the positive effects of the serum fraction of the invention.

Without being bound by theory this is possibly the mechanism behind the clinical observation that PRP augmented bone grafts have a markedly better 6-year result than decompression therapy in femoral head necrosis.

Specific method steps applicable in the present invention are as follows:
1. Obtain venous blood. No additives, e.g. anticoagulants, are necessary.
2. Remove red blood cells.
3. Obtain platelet rich fibrin (a yellowish coagulum floats on top of the red blood cell fraction).
4. From PRF separate the fluid fraction and the matrix (solid fraction). This can be done by pressing (squeezing) the PRF or by centrifugation at an increased, appropriate force.

In a preferred embodiment spinning down is carried out within 20 minutes, preferably within 15, 10, 5 minutes, or shorter period from obtaining venous blood.

Preferably, centrifugation is carried out at 1000 to 5000 g, preferably at 2000 to 4000 g, more preferably at about 3000 g. Preferably, centrifugation is carried out for 2 to 20 minutes, preferably for 4 to 15 minutes, highly preferably to about 10 minutes (+1-2 minutes).

The clot obtained (i.e. the coagel) can be removed by any appropriate method, e.g. by filtering or other physical means. In a preferred embodiment continuous centrifugation is applied and the clot is removed at an opening on the wall of the centrifugation space.

The fluid fraction from the clot can be removed by squeezing, pressing, filtering, vacuum filtering or any other appropriate method.

The invention is particularly useful in helping, facilitating or allowing the regeneration of the bone tissue of a subject. Bone tissue can be acutely damaged such as in case of trauma or surgery or can be chronically impaired eg. in case of degenerative bone diseases such as osteoarthrosis, bone necrosis, or bone ischemia. As an example, ischemia can be present during transplantation of bone tissue or organs containing bone such as osteochondral plugs. Specific methods, which can be improved by using the serum fraction of the invention, are e.g. methods to apply plasma preparations in surgery such as taught in the following publications.

Jun Araki ez al: Optimized Preparation Method of Platelet-Concentrated Plasma and Noncoagulating Platelet-Derived Factor Concentrates: Maximization of Platelet Concentration and Removal of Fibrinogen (Tissue Eng Part C Methods. 2012 March; 18(3): 176-85).

Dohan D. M. E et al.: Platelet-rich fibrin (PRF): A second-generation platelet concentrate. Part I: Technological concepts and evolution. Oral Surg Oral Med Oral Pathol Oral RadiolEndod 2006; 101:E37-44.

The foregoing description will be more fully understood with reference to the following examples. Such examples are, however, merely representative of methods of practicing one or more embodiments of the present invention and should not be read as limiting the scope of invention.

EXAMPLES

Example 1: Platelet-Rich Plasma as an Adjuvant Therapy in Aseptic Femoral Head Necrosis In a retrospective clinical observational study two surgical treatments were compared for avascular femoral head necrosis. Patients of the control group (n=13) were treated with core decompression alone, in the PRP group (n=19) core decompression was completed with the impaction of autologous bone chips mixed with autologous PRP. In the clinical observational study six years after the operation the PRP group had significantly lower failure rate (21% vs 67%, p<0.05) indicated by prosthesis implantation.

However, the exact role and cellular mechanisms are unknown and further data are necessary to prove the effect of the method.

Example 2: Preparation of an SPRF Composition, which is an Exemplary Serum Fraction of the Invention A preparation was prepared which was free of platelets, however was rich in platelet-derived factors.

The description of the procedure applied is as follows:
1. Venous blood was drawn into a standard, native tube without any additives.
2. Spinned it down instantly, preferably within 3 minutes, in a centrifuge at 1600-1700 G, for 5-10 minutes.
3. The red blood cells were collected at the bottom of the tubes, a yellowish coagulum floats on top of the red blood cell fraction in clear plasma. This clot (coagulum or coagel) was removed with a forceps and put on a clean petri dish.
4. The clot was gently squeezed to obtain the fluid out of the clot: The fluid obtained from the clot is essentially the final SPRF composition. As an estimate 0.4 ml final product can be gained from 6 ml of blood.

In order to speed up the clotting mechanism a silica-coated blood collection tube or a glass tube can also be used for drawing blood.

Example 3: Bone Explants and Oxygen Glucose Deprivation (OGD)

In this in vitro study, bone samples were obtained from the removed femoral head during total hip replacements for primary osteoarthritis. Femoral heads were obtained from patients suffering from coxarthrosis and undergoing hip replacement surgery, during which the femoral head is extracted in its entirety and discarded as surgical waste.
- Average 0,004 g weight explants (n=40 pieces/patient) were harvested from the femoral heads
- The explants were transported into cell culture conditions at 37° C. in Dulbecco's Modified Eagle Medium containing 1 g/l glucose, 5% Penicillin-streptomycin and 10% fetal bovine serum (Stem cell medium).

After an incubation of 3 days of the femoral heads oxygen-glucose deprivation (OGD) was used to model the poor circulation of the femoral head. At a tissue level OGD models cellular damage and impaired regeneration which is characteristic for degenerative bone diseases such as aseptic necrosis, osteochondrosis, osteoarthrosis, etc. The femoral heads were placed into glucose and amino-acid free medium at an oxygen level of $O_2$<0.5 mmHg (replaced with N2 gas). The tests have been continued at 1, 2.5, 3.5, 4, 5, and 7 hours after which the normal cell culture conditions were restored.

For qualitative testing of cell viability live and dead cells were labeled with Calcein-AM (488 nm) and Ethidium-Homodimer-2 (546 nm) fluorescent dyes, then evaluated by confocal microscopy (ZEISS LSM confocal microscopy, 20×).

For quantitative analysis of cell viability the methyl-thiazol-tetrasolium (MTT) assay was used with the following parameters: 1 h incubation in MTT solution, 1 h solubilization in isopropanol, absorbance measures at 570 and 690 nm, corrigated with the dry weight of bones. Assay was carried out at 37° C. In preliminary experiments, incubation was tested for 10 minutes 1, 2, 5 hours, and solubilization in isopropanol was tested for 10 minutes, 1, 2, 3, 4, 5, 6, 20 hours.

Example 4: Preparation of an Exemplary Serum Fraction of the Invention (SPRF) and its Characterization Platelet-rich plasma was isolated by the double-centrifugation protocol. Blood from healthy adult donors was collected in EDTA tubes (BD Vacutainer®, K2E EDTA) and centrifuged at 1300 rpm (320 g) for 12 minutes. The supernatant was removed and centrifuged at 3000 rpm (1710 g) for 10 minutes. The pellet was resuspended in stem cell medium at a 1:4 ratio during the OGD therapy and after that. Heparinized PRP was created by adding 100 μl fractionated heparine (Clexane 4000 NE/0.4 ml) to 1200 μl PRP after the isolation. Platelet-rich fibrin was prepared by centrifugation without anticoagulants for 5 minutes at 3000 rpm (1710 g). A fibrinous gel was removed from the tube and the fluid gently squeezed out of the gel to obtain isolated SPRF, which was added to the stem cell medium in 1:4 ratio. The concentration of serum was about 1:500 in case of PRP (500 μl of final product from 6 ml of blood) and about 1:600 SPRF (600-800 μl of final product from 6 ml of blood).

Example 5: Effect of Serum Fractions on Bone Explants after Oxygen Glucose Deprivation Bone explants were harvested from the discarded femoral heads from patients undergoing hip replacement. Bone grafts of about 10 mm$^3$ were collected and transferred immediately into Dulbecco's Modified Eagle Medium containing 1 g/l of glucose, 1% penicillin-streptomycin, and 10% fetal bovine serum. The explants were cultured in this medium under standard cell culture conditions in 24-well plates. Oxygen-glucose deprivation (OGD) was performed in a Pecon incubation system (Erbach-Bach, Germany) on the third day after explantation. The bone pieces were transferred into stem cell medium lacking glucose and amino acids and the oxygen was flushed with nitrogen to 0.5% $O_2$ level for 7 hours. After completion of OGD the medium was replaced and the explants were cultured in 20% oxygen and 5% 002. Blood fractions were added to the medium in a ratio of 1:4 just before OGD and was refreshed at medium changes. Both PRP and SPRF was prepared fresh just before use and never stored or frozen.

The grafts were incubated in a 1:9 diluted mixture of 3-(4,5-Dimethyl-2-thiazolyl)-2,5-diphenyl-2H-tetrazolium bromide (MTT, #M5655, Sigma) and stem cell medium at 37° C. for 60 min then diluted with isopropanol. Absorbance of the solution was measured by a PowerWave™ XS spectrophotometer at 570 nm and noise was filtered out by measuring the absorbance at 690 nm. The MTT-assay was performed on the third and sixth days after OGD.

There were only a few living cells on the bone chips on the day of the operation, and these cells were damaged. The samples were obtained from different patients. To get the various bone chips into a similar state, they were incubated in stem cell medium at 37° C. and 5% $CO_2$ for 3 days. Sufficient number of cells were detected on the $3^{rd}$ day, therefore OGD was started to model the ischemic condition. Based on the data of four patients significant difference was shown by t-test between cell viability of the bone chips on the day of surgery and after 3 days of incubation (81.75±47.72 vs. 106.28±55.24).

To achieve the ischemic state OGD was applied for many different intervals. Bone samples were observed for one, two and a half, three and a half, five and seven hours of OGD. After the OGD treatment lasting 5 hours, cell viability of the OGD treated and untreated groups were determined by MTT assay and it was found that 5 hours of treatment is not enough to damage cells (n=12 explants/groups, control: 50.36±6.66 vs. OGD: 36.97±3.00, t-test, not significant). Before OGD healthy adherent cells could be seen in green, and with increasing the time of OGD to 7 hours these cells lost their branches, changed their shape, got damaged or killed, so their color turned red. Significant difference was shown between the control group and the OGD-treated group by our quantitative measurement.

During the PRP treatment explants of the treated group received a mixture of PRP and stem cell medium in a 1:4 ratio.

PRP can not improve the viability of the cells after the ischemic condition (FIG. 2). As PRP was put into the stem cell medium, red blood cells in PRP were coagulated and the consistence of the solution became jelly-like. To avoid this consistency heparin was put into the PRP solution and cell viability was examined based on the protocol described earlier. A tendential growth was observed on the 6th day after the OGD compared to the untreated group, but this was not significant. Significant difference was not observed after testing the PRP in higher and lower concentrations (FIG. 2.). To activate platelets, three methods were tried: freeze and thaw, added $CaCl_2$ or $CaCl_2$ and thrombin, but none of them changed the earlier results (FIG. 2.).

The effect of SPRF during the OGD was examined. Treated explants were incubated in stem cell medium containing SPRF 1:4 scale for 7 hours. Based on the result of MTT assay, it is concluded that the group treated with SPRF did not have higher cell viability compared to the untreated group. SPRF cannot protect the immediate, acute effect of OGD (Data from 2 patients, control group: 70.18±6.64, OGD group: 24.85±2.49, SPRF group: 26.78±3.49, not significant difference).

After that long-term effect of SPRF was examined. Explants were treated during OGD and continuously for 6 days after OGD. On the 3rd day the medium was changed and cell viability assay was done and tendencial growth was shown in the SPRF-treated group. After another 3 days of incubation after the OGD the difference was significant (FIG. 3.).

In the pre-treated groups explants have received SPRF from the day of the surgery. In these cases the positive effect of SPRF can be declared, because significant difference was already detected between the treated and untreated groups after 3 days of OGD (4 patients, n=24 explants/groups, :$p<0.01$), which difference was more pronounced on the 6th day after OGD (4 patients, n=24 explants/groups, *: $p<0.0001$) (FIG. 3).

In our study two rather similar blood fractions were compared in a model of bone ischemia. Unexpectedly, a positive effect from PRP could not be observed even at high concentrations, while SPRF significantly improved the proliferation capacity of osteoblast cells damaged by ischemia. It is also of note that the proliferative effect was additive to the effect of FBS, a normal constituent of stem cell culture media, and was only observed at the postischemic state.

Example 6: Analysis of the Composition of Serum Fractions

For determination the growth factors and angiogenesis-related proteins in the SPRF and PRP Proteome Profiler Human Angiogenesis Array Kit (R&D System, #ARY 007) was applied and Adobe Photoshop was used for quantitation of protein expression. For the quantitative determination of platelets and ions in SPRF Sysmex XT 4000i and Beckman Coulter AU5800 was used. Results are reported as mean±SEM. Statistical significances were determined by t-test or one-way ANOVA with Tukey's post-hoc tests as appropriate with the Graphpad Prism software. Significance values of $p<0.05$ were considered significant.

TABLE 1

Laboratory parameters of blood fractions. Salts and proteins were measured by a Sysmex XT 4000i device. cell counts were determined by a Beckman Coulter AU5800 device. Data is presented as average ± SEM, n = 3.

|  | SPRF | PRP | PPP | normal range in whole blood | unit |
| --- | --- | --- | --- | --- | --- |
| Sodium | 141.00 ± 0.58 | 138.33 ± 0.67 | 139.00 ± 1.00 | 133-146 | mmol/l |
| Potassium | 4.04 ± 0.19 | 4.38 ± 0.26 | 3.90 ± 0.19 | 3.5-5.3 | mmol/l |
| Calcium | 2.31 ± 0.01 | 2.33 ± 0.04 | 2.30 ± 0.02 | 2.12-2.57 | mmol/l |
| Magnesium | 0.84 ± 0.01 | 0.88 ± 0.04 | 0.83 ± 0.00 | 0.6-1.1 | mmol/l |
| Chloride | 105.67 ± 0.88 | 103.00 ± 0.58 | 102.67 ± 0.88 | 99-111 | mmol/l |
| Phosphor | 1.21 ± 0.08 | 1.31 ± 0.08 | 1.16 ± 0.08 | 0.87-1.45 | mmol/l |
| Glucose | 5.36 ± 0.32 | 4.61 ± 0.34 | 5.26 ± 0.3 | 3.6-6.0 | mmol/l |
| Total protein | 74.87 ± 1.53 | 75.77 ± 1.7 | 74.03 ± 2.4 | 60-80 | g/l |
| Albumin | 49.67 ± 0.07 | 48.27 ± 0.33 | 47.57 ± 0.82 | 35-52 | g/l |

TABLE 1-continued

Laboratory parameters of blood fractions. Salts and proteins were
measured by a Sysmex XT 4000i device. cell counts were determined by a Beckman
Coulter AU5800 device. Data is presented as average ± SEM, n = 3.

|  | SPRF | PRP | PPP | normal range in whole blood | unit |
| --- | --- | --- | --- | --- | --- |
| IgG | 12.04 ± 1.34 | 10.22 ± 1.17 | 12.95 ± 1.17 | 6.9-14 | g/l |
| Hemoglobin | 0.00 ± 0.00 | 6.33 ± 0.88 | 0.33 ± 0.33 | 115-155 | g/l |
| Fibrinogen | 0.00 ± 0.00 | 1.07 ± 0.09 | 0.00 ± 0.00 | 1.5-4 | g/l |
| Red blood cells | 0.00 ± 0.00 | 0.28 ± 0.04 | 0.00 ± 0.00 | 4.2-6.1 | T/l |
| White blood cells | 0.01 ± 0.01 | 14.85 ± 2.61 | 0.01 ± 0.01 | 4.8-10.8 | G/l |
| Platelets | 1.33 ± 0.33 | 242.33 ± 75.9 | 16.00 ± 4.93 | 150-400 | G/l |

There are several key differences between PRP and SPRF measured by the proteome profiler assay (FIG. 4). The differences between the two fractions are limited to a handful of proteins, and it is a straightforward explanation that those factors that have higher levels in the SPRF fraction are responsible for the effect. It is noted that the full proteomics analysis of platelet release has just been compiled and it contains 3500 proteins, significantly more than those measured by the Proteome Profiler assay. However, two important proteins are often overlooked in these analyses: albumin and fibrin (Table 1.). Both proteins are abundant in serum and have rather well-described effects on cell proliferation. It was previously described that the in vitro and in vivo bone inducting effects of serum albumin, which raises the possibility that albumin itself is the active factor in PRP and SPRF. However, since albumin is present in both PRP and SPRF at comparable levels, plus it is also added to the culture medium in the form of FBS, it is concluded that it would not be responsible for the effects of SPRF observed in the current study.

A clear difference between PRP and SPRF preparations is the presence of fibrin (Table 1). Fibrin or the inactivated form fibrinogen is the second most abundant protein in serum and is present in both native and heparinized PRP while it is missing in SPRF. Several studies described that fibrin has a very strong pro-inflammatory reaction by specifically activating macrophages. Fibrin is also known as a key factor in the bone healing process after a fracture as the first step of enchondral bone formation. Although not all details of the cellular connections of fibrin is clear, it is reasonable to hypothesize that it is at least partly responsible for the differences in the proliferative action of SPRF versus PRP. It is also of importance that the model used in the present study is not designed to mimic bone healing under normal conditions, but rather regeneration potential of a damaged tissue. While the inflammatory response during an acute injury of a broken healthy bone may be beneficial, it has an opposite effect in a degenerative tissue where the remodelling capacity of the cells is impaired. It is believed that the current model resembles this later situation by mimicking an ischemic period. The observation that serum fractions had no effect on the "healthy" state of the bone explants but in the postischemic period also supports the idea that the current model, with its limitations as an ex vivo system, more resembles degenerative bone tissues. Furthermore, since the bone stock was femoral heads explanted at total hip replacement procedures in end-stage osteoarthosis, the current results should be interpreted in this context.

It is concluded that isolating serum from platelet rich fibrin has unique regenerative properties in damaged bone tissues. The isolation of SPRF is a simple procedure which can be performed at the bedside, providing an autologous mix of growth factors which may even be used in degenerative bone diseases. The fact that SPRF is devoid of fibrin and has generally fewer constituents than PRP, but better effects in this specific case is a further step in the standardization of serum products. Based on the current ex vivo human study, the clinical translation of the use of SPRF is initiated in degenerative and ischemic bone diseases.

The short term safety of PRP is well-established by numerous clinical studies, however, concerns emerged regarding its efficacy. Attempts at compiling a meta-analysis face the problem of non-standardized nomenclature, diverse isolation protocols and treatment regimens. Even well-designed studies focusing on a niche indication struggle with the very high variation of growth factor levels in PRP. Since PRP is essentially a mixture of known and yet unknown active agents, it is not evident which can be used as a reference compound for dosing. Therefore, currently the best way of standardization is defining the product by the isolation protocol rather than its constituents.

Example 7: SDF-1 Determination in SPRF

SDF-1 (Stromal cell-derived factor-1), also known as PBSF (pre-B-cell growth-stimulating factor), is a recently discovered protein belonging to the alpha chemokine (CXC) family of cytokines. SDF-1alpha and SDF-1beta are the first cytokines initially identified using the signal sequence trap cloning strategy from a human bone-marrow stromal cell line. SDF-1 has chemotactic activity on resting T lymphocytes and monocytes. The SDF-1 ELISA (Enzyme-Linked Immunosorbent Assay) kits [Sigma-Adrich, RAB0123, Human SDF 1 alpha ELISA Kit and RAB0124 SIGMA Human SDF-1 beta ELISA Kit] are in vitro enzyme-linked immunosorbent assays for the quantitative measurement of human SDF-1 in plasma (serum samples are not recommended for use in this assay as human SDF-1 concentration is low in normal plasma, it may not be detected in this assay), cell culture supernatants, and urine. This assay employs an antibody specific for human SDF-1 coated on a 96-well plate. Standards and samples are pipetted into the wells and SDF-1 present in a sample is bound to the wells by the immobilized antibody. The wells are washed and biotinylated anti-human SDF-1 antibody is added. After washing away unbound biotinylated antibody, HRP-conjugated streptavidin is pipetted to the wells. The wells are again washed, a TMB substrate solution is added to the wells and color develops in proportion to the amount of SDF-1 bound. The Stop Solution changes the color from blue to yellow, and the intensity of the color is measured at 450 nm. The standard dilution curve was prepared using the following SDF-1 concentrations (pg/ml): 6000, 3000, 1500, 750, 375, 187.5, 93.75.

The invention claimed is:

1. A pharmaceutical preparation comprising a blood-derived serum product which is an isolated serum fraction of platelet rich fibrin (PRF) said blood-derived serum product being contained in an application device for administration of the serum fraction to an individual and being obtained by a method comprising the steps of:
   a. separating and removing the red blood cell fraction from a venous blood sample without the addition of an anticoagulant to provide a plasma;
   b. clotting said plasma spontaneously by centrifugation carried out at 1000 to 5000 g to obtain a coagel of PRF and a supernatant, wherein in said method the centrifugation is carried out for 2 to 20 minutes;
   c. pressing or squeezing the coagel to obtain a fluid fraction which comprises an activated platelet releasate from the coagel, wherein said isolated serum fraction of PRF contains the fluid fraction; and
   d. providing the serum fraction in a pharmaceutical preparation which is contained in an application device for administration of the serum fraction to an individual, said serum fraction comprising a platelet releasate from activated platelets, wherein said isolated serum fraction of PRF comprises a reduced content of red blood cells, platelets or fibrinogen as compared to whole blood or a reduced content of fibrin as compared to said plasma, and
wherein said serum fraction of PRF is depleted in PDGF-AB, PDGF-BB and TGF beta-1 as compared to said plasma or whole blood, and has a non-inflammatory blood factor profile, and a non-differentiating but cell proliferating profile on osteoblasts.

2. The pharmaceutical preparation of claim 1, wherein in said method the centrifugation is carried out for 5 to 10 minutes.

3. The pharmaceutical preparation of claim 1, wherein in said method the centrifugation is carried out at 1600 to 2000 g.

4. The pharmaceutical preparation of claim 1, wherein in said method the centrifugation is carried out within 20 minutes from collecting venous blood.

5. The method of claim 1, wherein the the venous blood is collected from a single donor.

6. The pharmaceutical preparation of claim 1, wherein the blood is collected in a clot tube or syringe.

7. The pharmaceutical preparation of claim 1, wherein the serum fraction is prepared in a period up to 10 hours without adding preservatives.

8. The pharmaceutical preparation of claim 1, wherein said isolated serum fraction of PRF further contains at least one of angiogenesis or growth factor proteins selected from the group consisting of Activin-A, ADAMTS-1, Angiogenin, CXCL16, DPPIV, Endoglin, Endostatin/Collagen XVII, FGF-4, GM-CSF, HB-EGF, HGF, IGFBP-1, IGFBP-2, IGFBP-3, IL-1p, IL-8, Leptin, MCP-1, MMP-8, MMP-9, NRG1-31, Pentraxin-3, PD-ECGF, PlGF, Prolactin, TIMP-4, Thrombospondin-1, and uPA.

9. The pharmaceutical preparation of claim 1, wherein said isolated serum fraction of PRF is at least 1.2-fold enriched in Platelet factor 4, Serpin EI, or TIMP-1 as compared to said plasma or whole blood.

10. The pharmaceutical preparation of claim 1, is further depleted in at least one of angiogenesis or growth factor related proteins selected from the group consisting of SDF-1, Angiopoietin-1, EGF, VEGF, as compared to said plasma as provided in step a) or whole blood, wherein said SDF-1 concentration is less than 50% (w/w) of the concentration as compared to said plasma having a platelet concentration above baseline or whole blood.

11. The pharmaceutical preparation according to claim 1, said pharmaceutical preparation comprising a pharmaceutically acceptable carrier and an additional active substance and/or device to promote wound healing, cell proliferation or regeneration, wherein the additional active substance is a hydrogel, a tissue sealant or an active component thereof, wherein the device is a bone graft material and which preparation is contained in a syringe.

12. The pharmaceutical preparation of claim 1, wherein the serum fraction is produced in the application device in an aseptic way for direct administration to an individual.

13. The pharmaceutical preparation of claim 12, wherein the application device is also used as a preparation device both for collecting blood and for preparing the serum fraction.

14. The pharmaceutical preparation of claim 1, wherein the serum fraction is produced in a sterilized preparation device which allows aseptic collection of blood and aseptic transfer of the prepared serum fraction to the application device for administration to an individual.

15. The pharmaceutical preparation of claim 1, wherein the application device is a syringe.

16. The pharmaceutical preparation of claim 1, wherein the application device is a bone graft material.

17. The pharmaceutical preparation of claim 1, wherein the serum fraction includes the supernatant of the coagel.

18. The pharmaceutical preparation of claim 1, wherein the serum fraction prepared ready-to-use for the purpose of treating a patient without using a preservative.

19. The pharmaceutical preparation of claim 1, wherein the serum fraction is prepared in a preparation device which is suitable for aseptic collection of the blood and obtaining the isolated serum fraction and wherein the isolated serum fraction is aseptically transferred to the application device.

20. The pharmaceutical preparation of claim 1, wherein the serum fraction is storage stable frozen
   at 2° C.-12° C. for up to 24 months, or
   at −80° C. to −25° C. for up to 5 years.

21. An application kit comprising the components
   a. the pharmaceutical preparation of claim 1;
   b. an application device.

22. The application kit of claim 21 wherein the application device is a bone graft material, a gelling agent, a tissue sealant or an active component thereof; and
   optionally the application kit also comprises a device for mixing the pharmaceutical preparation of claim 1 and the application device to obtain a mixture ready for application.

* * * * *